United States Patent [19]

Moore-Ede et al.

[11] Patent Number: 5,433,223
[45] Date of Patent: Jul. 18, 1995

[54] METHOD FOR PREDICTING ALERTNESS AND BIO-COMPATIBILITY OF WORK SCHEDULE OF AN INDIVIDUAL

[76] Inventors: Martin C. Moore-Ede, 110 Hundreds Rd., Wellesley Farms, Mass. 02181; Ross E. Mitchell, 4 Allston St., West Newton, Mass. 02165-2554

[21] Appl. No.: 154,359

[22] Filed: Nov. 18, 1993

[51] Int. Cl.⁶ .............................................. A61B 19/00
[52] U.S. Cl. ................................................... 128/898
[58] Field of Search ................. 128/630, 731, 732, 898

[56] References Cited

U.S. PATENT DOCUMENTS

| | | | |
|---|---|---|---|
| 3,877,466 | 4/1975 | Montor | 128/732 |
| 4,104,621 | 8/1978 | Yanagishima et al. | 340/576 |
| 4,397,531 | 8/1983 | Lees | 351/210 |
| 4,540,979 | 9/1985 | Gerger et al. | 340/576 |
| 4,845,625 | 7/1989 | Stannard | 364/407 |
| 5,111,391 | 5/1992 | Fields et al. | 364/401 |
| 5,140,562 | 8/1992 | Moore-Ede et al. | 368/62 |
| 5,176,133 | 1/1993 | Czeisler et al. | 128/395 |
| 5,311,877 | 5/1994 | Kishi | 128/732 |

OTHER PUBLICATIONS

"An Algorithm for Shift Scheduling which Considers Circadian Principles" Kostreva et al., Intl. Journal of Industrial Ergonomics, 7 (1991), pp. 317–322.
"Rhythms in Sleep and Fatigue—A Model", Åkerstedt and Folkard Abstract of 32nd Congress of Intl. Union of Physiological Sciences, Aug. 1993—Glasgow.

*Primary Examiner*—Ruth S. Smith
*Attorney, Agent, or Firm*—David R. Pressman

[57] ABSTRACT

A method enables the prediction of the likely alertness level of an individual at a given point in time based upon the analysis of certain biological and other parameters associated with the individual subject including, circadian phase of the biological clock, accumulated acute or chronic sleep deprivation, shift commencement and termination time, time of last sleep, environmental light, etc. Among other advantages, the method facilitates the creation of bio-compatible schedules for shift workers by providing an accurate model of the likely alertness level of the individual on a specific schedule.

15 Claims, 14 Drawing Sheets

Fig. 6A

| OFFSET | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| TIME | 00:00 | 00:30 | 01:00 | 01:30 | 02:00 | 02:30 | 03:00 | 03:30 | 04:00 | 04:30 | 05:00 | 05:30 | 06:00 | 06:30 | 07:00 | 07:30 |
| FACTOR | .49 | .42 | .4 | .39 | .38 | .37 | .37 | .36 | .36 | .35 | .25 | .25 | .31 | .44 | .61 | .75 |

| OFFSET | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|
| TIME | 08:00 | 08:30 | 09:00 | 09:30 | 10:00 | 10:30 | 11:00 | 11:30 | 12:00 | 12:30 | 13:00 | 13:30 | 14:00 | 14:30 | 15:00 | 15:30 |
| FACTOR | .85 | .84 | .81 | .69 | .66 | .63 | .61 | .60 | .60 | .58 | .55 | .45 | .42 | .40 | .42 | .52 |

| OFFSET | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|
| TIME | 16:00 | 16:30 | 17:00 | 17:30 | 18:00 | 18:30 | 19:00 | 19:30 | 20:00 | 20:30 | 21:00 | 21:30 | 22:00 | 22:30 | 23:00 | 23:30 |
| FACTOR | .65 | .74 | .83 | .86 | .89 | .92 | .95 | 1.0 | .95 | .92 | .84 | .80 | .68 | .65 | .61 | .51 |

Fig. 6B

| OFFSET | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| TIME | 00:00 | 00:30 | 01:00 | 01:30 | 02:00 | 02:30 | 03:00 | 03:30 | 04:00 | 04:30 | 05:00 | 05:30 | 06:00 | 06:30 | 07:00 | 07:30 |
| FACTOR | .37 | .32 | .28 | .24 | .20 | .16 | .15 | .15 | .14 | .13 | .10 | .08 | .06 | .04 | .03 | .03 |

| OFFSET | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|
| TIME | 08:00 | 08:30 | 09:00 | 09:30 | 10:00 | 10:30 | 11:00 | 11:30 | 12:00 | 12:30 | 13:00 | 13:30 | 14:00 | 14:30 | 15:00 | 15:30 |
| FACTOR | .03 | .03 | .03 | .03 | .03 | .03 | .03 | .03 | .03 | .03 | .03 | .03 | .03 | .03 | .03 | .03 |

| OFFSET | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|
| TIME | 16:00 | 16:30 | 17:00 | 17:30 | 18:00 | 18:30 | 19:00 | 19:30 | 20:00 | 20:30 | 21:00 | 21:30 | 22:00 | 22:30 | 23:00 | 23:30 |
| FACTOR | .03 | .03 | .03 | .03 | .03 | .03 | .03 | .03 | .03 | .03 | .03 | .03 | .03 | .03 | .45 | .41 |

| OFFSET | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| TIME | 00:00 | 00:30 | 01:00 | 01:30 | 02:00 | 02:30 | 03:00 | 03:30 | 04:00 | 04:30 | 05:00 | 05:30 | 06:00 | 06:30 | 07:00 | 07:30 |
| OFFSET | 16 | 17 | 18 | 19 | 20 | 21 | 22 | 23 | 24 | 25 | 26 | 27 | 28 | 29 | 30 | 31 |
| TIME | 08:00 | 08:30 | 09:00 | 09:30 | 10:00 | 10:30 | 11:00 | 11:30 | 12:00 | 12:30 | 13:00 | 13:30 | 14:00 | 14:30 | 15:00 | 15:30 |
| OFFSET | 32 | 33 | 34 | 35 | 36 | 37 | 38 | 39 | 40 | 41 | 42 | 43 | 44 | 45 | 46 | 47 |
| TIME | 16:00 | 16:30 | 17:00 | 17:30 | 18:00 | 18:30 | 19:00 | 19:30 | 20:00 | 20:30 | 21:00 | 21:30 | 22:00 | 22:30 | 23:00 | 23:30 |

Fig. 6C

| RESTRICT DAYS | 0 | 1 | 2 | 3 | 4 | 5 | 6 | 7 |
|---|---|---|---|---|---|---|---|---|
| FACTOR | 1.0 | .88 | .84 | .78 | .74 | .68 | .56 | .51 |

Fig. 6D

| SLDX | 0 | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| FACTOR | 8 | 7 | 6 | 5 | 4 | 3 | 2 | 1 | 0 | 1 | 2 | 3 | 4 | 5 | 6 | 7 | 8 |

Fig. 6E

METHOD FOR PREDICTING ALERTNESS AND BIO-COMPATIBILITY OF WORK SCHEDULE OF AN INDIVIDUAL

BACKGROUND—FIELD OF INVENTION

This invention relates to the prediction of the alertness level of an individual and the suitability of work schedules therefor, especially as related to a shift worker.

BACKGROUND—DESCRIPTION OF PRIOR ART

In the modern world, many organizations rely on around-the-clock operations. Airlines, railroads, nuclear power plants, to name just a few, are entities where safety is of great concern and where it is necessary to ensure staffing twenty-four hours a day.

With the advent of around-the-clock operations came the need for the development of shift work schedules as a way to address the requirement for staffing at all hours. It soon became apparent, however, that shift work brings with it its own set of problems. Shift workers often complain of inability to obtain adequate sleep during their off-hours, chronic sleep deprivation, reduced alertness, and even falling asleep on the job, as being realities of the around-the-clock workplace.

Besides the obvious effects on productivity caused by less than fully alert workers, there is also a grave safety concern caused by this situation. Accidents such as those which occurred at the nuclear power plants at Three Mile Island and Chernobyl, the chemical plant in Bhopal, and elsewhere have been directly linked to worker fatigue.

It is now accepted that it is critical to ensure that workers are fit for duty, especially those involved in industries where safety is a major concern.

In many cases, governments regulate the number of consecutive hours a person may work without time off as well as the minimum number of hours of rest between work shifts. These hours-of-service regulations were developed, for example, for airline pilots, truck drivers, and railroad engineers. The intent of these regulations is to ensure that workers are not excessively fatigued by their work hours and are sufficiently rested to be able to perform their work in a safe manner. The assumption is made, for example, that after 8 hours off between shifts, a truck driver is ready and fit to begin work again. Because they were developed in the early twentieth century, before any substantial scientific work on measuring circadian rhythms and alertness physiology had been undertaken, these regulations do not take into account many of the variations in alertness which are due to biological factors which are now known to have an important effect on alertness.

Various scheduling methodologies exist which take into account the availability of workers to perform a certain task at a given point in time. For example, in U.S. Pat. No. 5,111,391 to Fields et al. (1992), a system and method for making staff schedules as a function of available resources as well as employee skill level, availability, and priority is described. This system and method includes a database for storing and retrieving information characterizing various scheduling requirements. However, the incorporation of alertness factors is not included in this scheduling methodology. In fact, alertness forecast and consideration is completely absent from it.

Another system, described in U.S. Pat. No. 4,845,625 to Stannard (1989), allows the selection of airline flight groupings (bid packs) based on preferences of employees. Flights making up the bid packs, however, are not scheduled using any alertness forecasting methodology.

While sophisticated scheduling algorithms exist for devising flight bid packs which take into account optimal usage of aircraft and regulatory requirements for time off of workers, none of the existing methodologies take into account the alertness of the workers.

In recent years, the existence of an endogenous circadian pacemaker, also known as a biological clock, has been discovered to be part of every individual's brain. Through our understanding of the human biological clock, we now know that people experience predictable variations in alertness as a result of their positioning within the circadian cycle or circadian time-of-day.

In U.S. Pat. No. 5,140,562 (1992), to the present inventors, we disclose a Biological Timepiece which continuously calculates and displays the actual biological time of day of an individual based on a pre-determined rate corresponding to the rate at which time would progress in a free-running circadian clock for an individual. This rate is adjusted in real time based upon the absence or presence of clock-altering stimuli, such as bright light, so that the watch is able to continuously display the individual's accurate biological time. The watch does not predict the alertness level of an individual; it simply displays the individual's "biological" time of day.

Assessing biological time of day can also be accomplished through laboratory testing. For example, U.S. Pat. No. 5,176,133 to Czeisler et al.(1993), discloses a method of assessing the phase of the endogenous circadian pacemaker by eliminating activity-related confounding factors associated with the sleep-rest cycle in order to accurately measure core temperature variations as an indication of circadian phase. Czeisler also teaches a method of modifying the circadian pacemaker through the application of periods of bright light and/or darkness.

While knowing the initial positioning of the circadian pacemaker is necessary in order to predict alertness accurately, Czeisler does not in any way provide a method for predicting alertness. His methodology is for use in assessing and modifying the biological clock of an individual.

There exists a substantial body of information which allows for the reliable estimation of the initial circadian phase of an individual based on comparisons made to the body of normative data, or the literature in general, as stated by Czeisler. From that initial estimate, a baseline alertness curve can be made for an individual. However, the process of simulating the progress of the individual through various periods of sleep, work, and rest in order to predict alertness is not in any way addressed by Czeisler.

Making an assessment based on normative data of the alertness of an individual after several work periods is not reliable since each individual's schedule and habits are different and must be evaluated separately.

In 1977, a laboratory methodology for measuring sleep tendency was developed. This method, involving a test known as the Multiple Sleep Latency Test (MSLT), was developed by Mary Carskadon and William Dement at Stanford University. Although not ideal, it can be used to estimate alertness by measuring the amount of time it takes a subject to fall asleep in a darkened room, after having been asked to try to sleep. Detection of onset of sleep is made by means of EEG monitoring. If sleep is not detected after twenty minutes, the test is terminated and a score of twenty is assigned. Otherwise the number of minutes until sleep onset is recorded, and the subject is re-awakened. The test is typically given every two hours for the duration of the testing period.

The MSLT and its variants, such as the Repeated Test of Sustained Wakefulness (RTSW), and the Maintenance of Wakefulness Test (MWT), have been used as a means of estimating alertness, and they are in wide use in clinical testing situations. However, due to the lengthy nature of the test, and the complex monitoring equipment required, it is not practical nor is it intended to be used as a method of ongoing alertness monitoring.

Over the past fifteen years, a large number of studies have been conducted by sleep and alertness researchers to determine the influence of physiological, behavioral, and environmental factors on alertness. The influence of circadian time of day, hours of sleep, consecutive days of sleep restriction, consecutive hours of sleep deprivation, napping, light exposure, caffeine and alcohol ingestion, age, sleep disorders, rotating work shifts, and various other factors which affect alertness and sleepiness have been examined. However, none of these studies provides a method to predict the alertness of an individual or to design bio-compatible work shifts.

Devices exist to allow the monitoring of current alertness levels. For example, in U.S. Pat. No. 4,540,979, to Gerger (1985), a grip-responsive operator alertness monitor is described which includes a pressure sensor associated with a mechanism for controlling a vehicle. The pressure sensor detects operator fatigue as exhibited by a change in operator pressure on the control mechanism. An operator stimulus is coupled to the pressure sensor and, upon sensing fatigue, produces a stimulus such as a visual or audible alarm. Another device, disclosed in U.S. Pat. No. 4,397,531 to Lees (1983), determines whether an eye within a field of view is closed for a predetermined period of time. If so, the assumption is made that the subject has fallen asleep, so that corrective measures can be taken, such as the sounding of an alarm. A steering-wheel reversal driver alertness monitor is described in U.S. Pat. No. 4,104,621 to Yanagishima (1978). This device causes the steering wheel to vibrate when abrupt movements are detected, an indication that the operator is fighting sleep.

All of the above-referenced devices are designed to monitor current alertness level. None of them predict alertness in any way.

Another approach to ensuring safety on the job is through "fitness for duty" testing. Methodologies are being developed to permit the determination as to whether or not a given individual is ready and fit to perform a work shift. As with the alertness monitoring devices described above, this testing is used to determine alertness immediately prior to or during the work shift. It does not provide a method of predicting the likely alertness level of an individual over an extended period of time.

In a paper published in the International Journal of Industrial Ergonomics entitled "An algorithm for shift scheduling which considers circadian principles", by MM Kostreva, et al. (1991, Vol. 7, pg. 317-322), the authors present a method of shift scheduling based on known circadian principles, such as that shifts should rotate in a forward direction (i.e. day shift to evening and then to night shift), and that there should be a minimum of changing of workers' schedules from one shift to another. While this is a step in the right direction, no shift by shift analysis of the alertness level of individuals is provided or proposed.

A quantitative alertness modeling procedure has been developed by Akerstedt and Folkard. As described in the abstract of an oral presentation given at the 1993 Congress of the International Union of Physiological Sciences, this model predicts alertness (or sleepiness) "using the sum of three processes: S, W, and C. Process C represents sleepiness due to circadian influences and has a sinusoidal form. Process S is an exponential function of the time since awakening. Maximum alertness is reached upon awakening and alertness initially falls rapidly but levels off and gradually approaches an asymptote. At sleep onset process S is reversed (and called S') and recovery occurs as an exponential function that initially increases at a very rapid rate but subsequently levels off towards an upper asymptote. The final component is the wake-up process W, or sleep inertia, after forced awakenings, which is also exponential, but even steeper." The model outputs an alertness curve based on these computations.

The Akerstedt and Folkard model is a theoretical, mathematical approach to predicting alertness. It is centered around the existence of biological processes which, as such, have not been proven to exist in any biological organism. The mathematical model and the values of the theoretical processes are adjusted arbitrarily in order to get the results to agree with observation. As discussed in Moore-Ede and Czeisler "Mathematical Models of the Circadian Sleep-Wake Cycle" (Raven 1984), there are many such mathematical models which show superficial behavioral similarities to biological processes but ultimately are abandoned as additional scientific data from empirical observation show their inherent weaknesses.

What is needed is a method of predicting the alertness of an individual, based on alertness data which has been derived from empirical scientific measurement of alertness in subjects exposed to known real-world factors which affect alertness, and to be able to apply this knowledge of the individual's alertness to the planning of work schedules which will maximize safety by ensuring that an acceptable alertness level is maintainable throughout the work shift.

OBJECTS AND ADVANTAGES

Accordingly, one object of this invention is to provide a method to permit estimation of the probable level of alertness of an individual based on real-world factors affecting that individual.

A further object is to facilitate the evaluation of the bio-compatibility of work schedules for an individual based upon this prediction.

It is also an object to determine, after the fact, the likely alertness level of an individual at some time in the past based on historical data.

Another object is to provide a method which permits the development of new bio-compatible schedules for individuals by taking into account the likely alertness level of individuals working on various proposed schedules.

Further objects will become apparent from the ensuing description, claims and accompanying drawings.

GENERAL DESCRIPTION

In accordance with the present invention, a method of predicting the likely alertness level of an individual at a given point in time is provided. The method further defines a methodology for selecting bio-compatible schedules or evaluating the bio-compatibility of a schedule for the individual.

In order to determine the alertness level, the individual's Baseline Alertness Curve (BAC) is first as certained. The BAC represents the levels of alertness which a person would have at various specified times of day when he or she is not sleep deprived and is in an optimal state. For any individual, the Baseline Alertness Curve is primarily determined by his or her:
1. Age;
2. Home time zone;
3. Currently acclimatized work shift or sleep schedule, and the light-dark exposure schedule determined by the individual's work-rest schedule;
4. Morningness/eveningness tendency of the individual (Lark/Owl);
5. Any underlying sleep or circadian disorder pathology.

The BAC is, thus, the optimal curve that a person would display in a stable environment, with a stable work and sleeping schedule and with adequate sleep to remove any effects of sleep deprivation.

Stimuli which have an effect on human alertness are referred to as "alertness modifying stimuli" (AMS). In addition to the time of day on the circadian clock (the circadian phase or biological time-of-day), other AMS include acute or accumulated chronic sleep deprivation, environmental light, ingested nutrients and chemicals, sense of danger, interest, or opportunity, muscular activity, environmental sound, temperature, and aroma. Each of these stimuli act to a greater or lesser degree to affect the alertness level of an individual who experiences them. Some of the stimuli tend to affect only the level of the BAC, while others affect the phase, and some affect both.

For example, it is well known, through both extensive laboratory testing as well as common experience, that sleep deprivation results in decreased alertness. Our method allows for an adjustment to the alertness level based on the amount of sleep deprivation recorded. This is an example of a stimulus which affects the level of the BAC.

There are also stimuli which affect the phase of the BAC. For example, the effects of properly timed bright light on the circadian cycle of an individual will affect the phase of the circadian cycle of the individual. Obviously, the phase is directly related to the alertness level at any point of the BAC, so in order to predict alertness accurately, phase as well as other alertness modifying stimuli must be considered.

Once the BAC for an individual is known, various adjustments are applied to it in order to reflect the effect of the stimuli to which the user has been exposed.

One of the novel and beneficial features of our method is the use of "real-world" data not only as inputs to the simulation, but also as an integral part of the processing. For example, for input to the model, estimation of the sleep-wake schedules for employees can be made from payroll data which can be retrieved from existing computer files, without the need for manual estimation, calculation, or entry. Other subjective information, such as behavioral and sleep diary data, is used to provide a more complete picture of the actual exposure of subjects to AMS in real-world conditions. The processing methodology incorporates the empirically derived data from dozens of published and unpublished studies on the physiological, behavioral and environmental factors which influence a person's alertness and sleepiness, including the circadian time-of-day, hours of sleep during the prior sleep episode, consecutive days of sleep restriction, consecutive hours of sleep deprivation, and various other factors.

In one embodiment of the present invention, and as shown in the detailed explanation which follows, the effects of various AMS are represented as adjustment factors which are applied to the BAC in order to arrive at a Modified Baseline Alertness Curve (MBAC) for the individual. The MBAC represents the predicted alertness level for the individual when the effects of all available AMS have been applied. The output is then output in the form of an alertness chart or other alertness reference.

In another embodiment, the computed MBAC is compared to a proposed work schedule in order to determine whether the predicted alertness level is biologically compatible with the schedule. In other words, the alertness level at each point within the schedule is compared to a minimum acceptable level for the job to be performed. If the alertness level falls below the minimum threshold for an extended period during the proposed shift, the schedule is ruled out as biologically incompatible with the individual. Thus, in this embodiment, a plurality of existing schedules can be compared to the individual's MBAC in order to find those most compatible from an alertness standpoint.

In yet another embodiment, the computed MBAC is used to determine acceptable and/or optimal periods during which an individual might fulfill a work schedule. Using this predictive methodology, bio-compatible work schedules can be developed based on knowledge of workers' predicted alertness levels.

BRIEF DESCRIPTION OF THE DRAWINGS

FIG. 6A shows a Baseline Alertness Curve (BAC) as numeric values stored in an array.

FIG. 6B shows the effect of successive hours of sleep deprivation as numerical factors stored in an array.

FIG. 6C is an array containing the hours of the day in half-hour increments.

FIG. 6D shows the effect of successive days of reduced (restricted) sleep as numerical factors stored in an array.

FIG. 6E is a multiplier array used in selecting a specific alertness curve based on the number of hours slept prior to the current work shift.

FIGURE 1—HIGH LEVEL SCHEMATIC

FIG. 1 is a high level schematic diagram which illustrates the overall design of a Circadian Alertness Methodology according to the invention.

Figure 1:
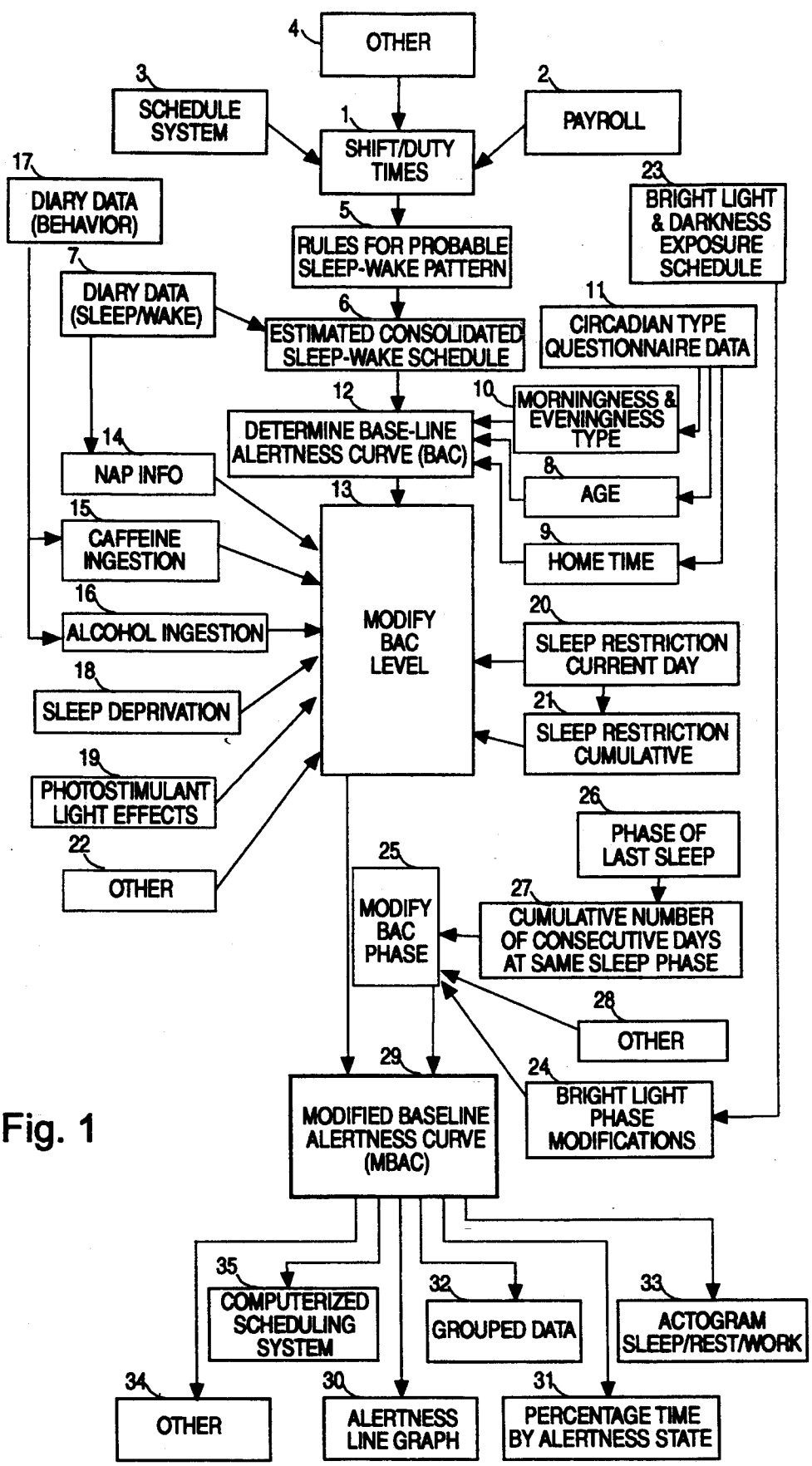
FIG. 1 is a high level schematic which illustrates the overall design of a Circadian Alertness Simulation (CAS) methodology in accordance with the present invention.

The shift or duty times for an individual 1 are determined through analysis of payroll 2, scheduling system 3, or other 4 (e.g., diary) data sources which may be available. In addition to the extraction of this information from existing data processing systems, this data may also be manually entered.

Diary data can be accumulated from records kept by the subject, by an observer, by an automated monitoring process, or developed through the investigation of a third party.

Rules for estimating the probable sleep-wake pattern for the individual 5 are applied to the shift/duty times 1 in order to arrive at an estimated consolidated sleep/wake schedule for the individual 6. This sleep/wake schedule may also be determined by using manually entered sleep/wake data, shown at 7, and in the detailed explanation which follows. The subject's age 8, home time zone 9, and morningness-eveningness status 10, determined from a Circadian Type Questionnaire 11, are evaluated with the estimated consolidated sleep/wake schedule 6 in order to arrive at a Baseline Alertness Curve (BAC) 12 for the individual. The BAC represents the alertness curve for the individual before application of the various Alertness Modifying Stimuli.

The BAC is modified [block 13] by applying various factors due to alertness enhancing or alertness impeding stimuli. Nap information 14 is ascertained from the Sleep/Wake Diary Data 7. In the present embodiment, a nap is considered to be any sleep period of up to three hours duration. Sleep in excess of three hours is considered "consolidated sleep." The nap information causes a modification to the BAC level 13, since a nap serves as a restorative alertness factor. In much the same way, caffeine ingestion 15 is read from the behavioral diary data 17 and modifies the alertness level. Alcohol ingestion data 16 is read from the behavioral diary data 17 and also modifies the BAC level; however, in this case, the level will be decreased due to the alertness impeding effects of alcohol. The sleep deprivation factor 18, which defines the state where the individual has not slept for a period exceeding 16 hours since the last consolidated sleep, also affects alertness level. (Note that the negative affects of consolidated sleep deprivation may be partially overcome by the alertness-enhancing effects of napping 14.) The effects of photo-stimulation (bright light, of insufficient intensity to materially affect the circadian phase but sufficiently bright to enhance alertness, shown in block 19) will also affect the BAC level. A sleep restriction day 20 is defined as a day during which the individual did not continuously sleep for at least six hours. The cumulative effect of successive days of sleep restriction, shown at 21, has an additional effect on the BAC level. Other alertness-altering stimuli 22 such as aroma, job stress factors, etc., which have an effect on alertness are also included to enable adjustment to the BAC level at a given time.

Exposure to high intensity bright light and to darkness, shown at 23, affects the circadian phase of the subject. The phase modification algorithm at 24, evaluates the effect of the exposure based on the current circadian phase of the individual at the time of exposure. It, subsequently, modifies the BAC phase of the individual (block 25) in accordance with known effects of light/darkness exposure. The phase of last sleep 26 is evaluated to determine if it is changing from the norm. If so, the effects of cumulative days at the same non-standard sleep phase 27 will also cause a BAC phase shift for the individual. Other phase-affecting stimuli 28, such as the effects of drug therapies (melatonin, etc.) can also have an effect on the BAC phase.

Figure 2:
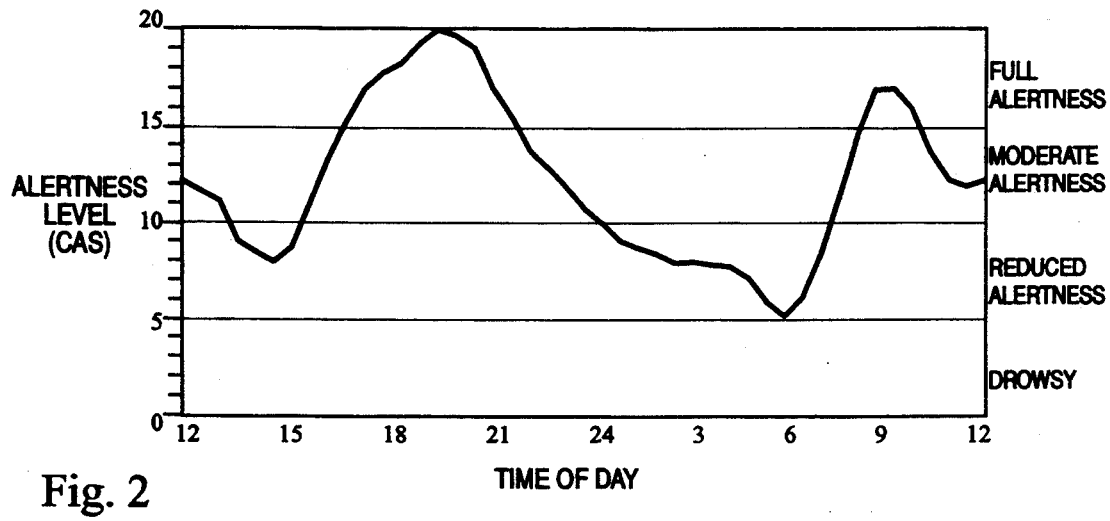
FIG. 2 illustrates the Baseline Alertness Curve (BAC) of a worker.

After application of all alertness-modifying stimuli for which information is available, a Modified Baseline Alertness Curve (MBAC) is determined. This curve represents the alertness level of the individual throughout the desired period, with all alertness-altering effects having been taken into account by the simulation methodology. The MBAC can then be supplied in any of several formats. It can be output as an alertness line graph 30. This format is shown in FIG. 2, described below. It can also be output as Percentage of time by alertness state (block 31). Data for many individuals can be grouped together and summarized (block 32). An actogram (sleep/rest/work) 33 or other output 34 can be supplied as well. Results can also be supplied to a computerized scheduling system 35 for use in selecting bio-compatible work schedules.

Not all data elements are required in order to perform the simulation. Indeed, in most cases, the simulation will most likely be performed with a subset of all possible elements.

FIGURES 2—BASELINE ALERTNESS CURVE

This figure shows the Baseline Alertness Curve (BAC) for a worker who is not sleep-deprived or restricted. The representation of alertness is done using a standard MSLT scale although alertness may be expressed on other scales. In this representation, alertness states are divided into four categories:

1. levels below 5 represent a dangerously drowsy state,
2. levels between 5 and 10 represent a state of reduced alertness,
3. levels between 10 and 15 represent a state of moderate alertness, and,
4. levels above 15 represent a state of full alertness.

This figure represents a normal alertness curve expected for an individual who is operating on a normal day schedule, without any alertness-modifying stimuli. It can be seen that the minimum alertness point is situated at approximately 5 AM, which coincides with the nadir of core body temperature. Alertness then varies throughout the day, dipping in the mid-afternoon, then rising again until reaching a peak at approximately 7 PM. Alertness falls off rapidly thereafter until again reaching the minimum just prior to the hour of normal wake-up. A normal wake up time of 6 AM is assumed in this baseline curve. This will be subsequently modified for the actual normal wake-up time for the individuals being studied.

It should be noted that the alertness levels shown assume an awake subject. Sleep latency testing (MSLT) throughout the night has demonstrated that this curve is an accurate representation of the approximate potential alertness level at any given point in time.

FIGURE 3—EFFECT OF SUCCESSIVE DAYS OF REDUCED SLEEP

Figure 3:
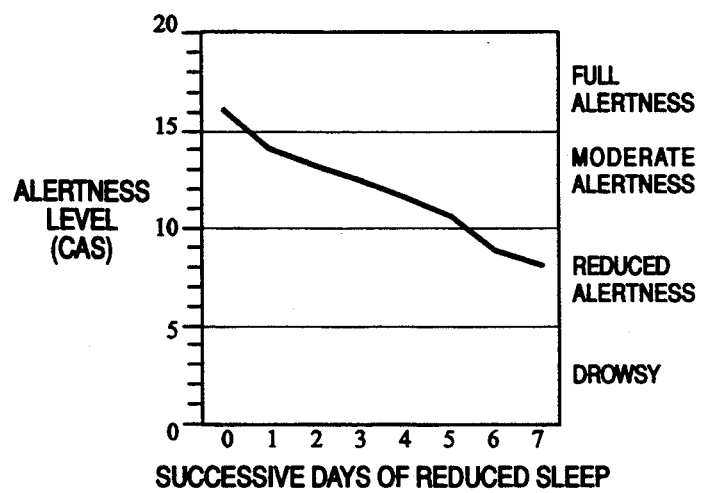
FIG. 3 illustrates the effects of successive days of reduced (restricted) sleep on the alertness of a worker.

Numerous factors affect the alertness level of a worker. In FIG. 3, the effect of successive days of reduced sleep is shown. As in the preceding figure, an MSLT representation is shown.

If a worker sleeps fewer than 6 hours on days prior to a work shift, this is referred to as "sleep restriction." Successive days of sleep restriction have been shown to affect daytime alertness.

FIG. 3 shows mean daytime alertness for a worker who sleeps fewer than 6 hours. It can be seen that after seven days of reduced sleep, alertness is severely affected. The Circadian Alertness Simulation (CAS) methodology takes into account the effects of sleep restriction, as will be explained.

FIGURE 4—EFFECT OF SLEEP DEPRIVATION

Figure 4:
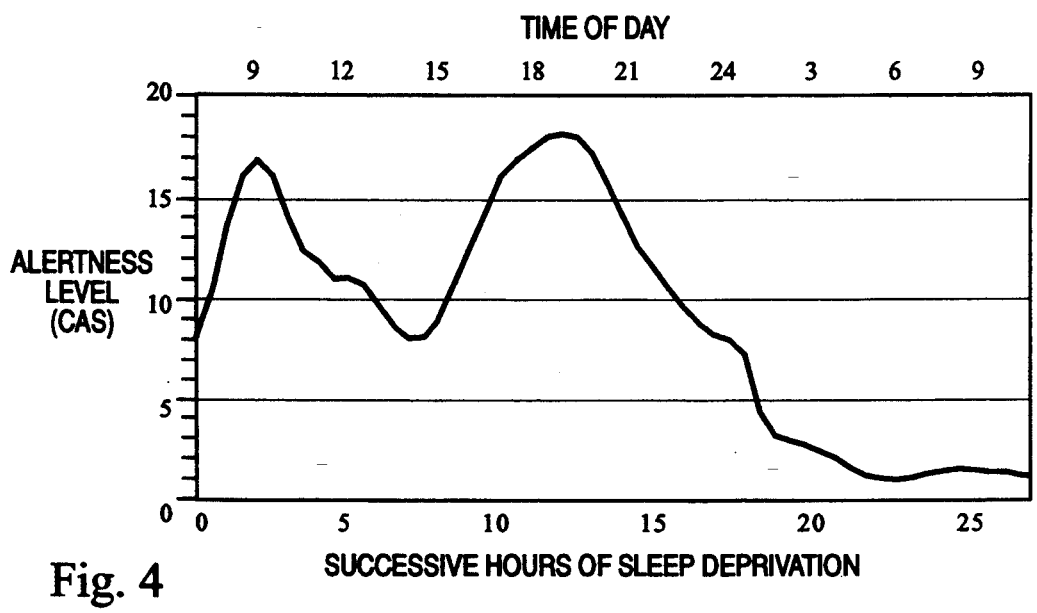
FIG. 4 illustrates the effect of successive hours of sleep deprivation on the alertness of a worker.

Another determinant of alertness is the hours since the last consolidated sleep, known as sleep deprivation. When an individual remains awake after his or her normal bedtime hour, that individual becomes increasingly drowsy in a predictable way. FIG. 4 shows the effect of successive hours of sleep deprivation on the alertness of an individual. This factor is also taken into account in the alertness simulation.

FIGURE 5—EFFECT OF HOURS SLEPT PREVIOUS NIGHT

Figure 5:
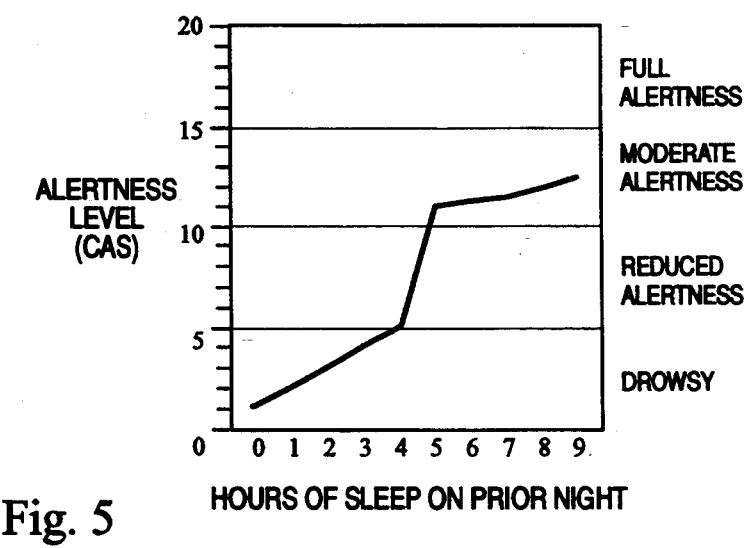
FIG. 5 illustrates the effect of the number of hours of sleep on the night preceding a work shift.

In FIG. 5, the effect of the number of hours slept the prior night is shown. It can be seen that with less than 4 hours sleep a worker can be expected to be very drowsy. Between 4 and 5 hours sleep, the negative effects on alertness subside rapidly, with smaller (although not insignificant) variations recorded between 5 and 9 hours. The effect of the number of hours slept the prior night is also taken into account in the circadian alertness simulation.

FIGURES 6A–6E—VALUES AS STORED IN ARRAYS

FIG. 6A shows the Baseline Alertness Curve values as stored in an array. The offset 0 represents midnight, with each entry being one half hour later than the previous entry. There are, consequently, 48 entries in the table. Access to this array will be made by offset based on time of day, as modified by the simulation.

FIG. 6B shows the alertness curve for a sleep-deprived individual. The format is the same as the array shown in FIG. 6A.

FIG. 6C contains all the hours of the day. This array is accessed to associate shift hours with wall clock hours in order to facilitate display of the data.

FIG. 6D shows the effect of successive days of sleep restriction on the alertness of an individual. The number of days of restricted sleep corresponds to the offset for accessing values in the array.

FIG. 6E is a multiplier array which is accessed based on the number of hours of consolidated sleep which the worker experienced prior to beginning the current work shift. This array is used to enable the selection of an appropriate alertness curve for the individual.

FIGURES 7A–7H—GENERAL DISCUSSION

The method of the present invention utilizes a computer program as illustrated by the flowcharts in FIGS. 7A through 7H. These drawings describe the processing steps for determining the likely alertness level of an individual operating on a given work schedule, with known sleep and wake patterns.

For simplicity of explanation in the present embodiment, all times are expressed as numbers from 0 to 23.5, in half-hour increments of 0.5. For example, 6:30 PM would be expressed as 18.5; however, any other time representation method can be used and converted to convenient numerical form in a straightforward manner, commonly known to those skilled in the art of computer programming.

In addition, proper computation of the difference between days is assumed to be taken into account through conventional programming methodology. For example, while an actual sleep onset time of 23 (11 PM) appears "later" than the actual wake time of 7 (7 AM), this simply means that the sleep onset time occurred on the day prior to the wake up. The worker will not have slept more than 24 hours at a time, so computation of the actual number of hours slept (8) is a straightforward matter.

Alertness in this example, is presented as a standard MSLT score although any representation of alertness can be expressed by the methodology.

The abbreviations used in the diagrams are as follows:

| | |
|---|---|
| ALT | Alertness Level Matrix |
| AS | Actual Sleep Onset Time |
| AW | Actual Wake time |
| CDSR | Consecutive Days of Sleep Restriction |
| CP | Current Period Being Evaluated |
| CTB | Count in ½ hour ticks until Normal Bedtime |
| D | Sleep-Deprived Alertness Value for Current Period |
| DDF | Deprived Day Factor Array |
| DEPSET | Sleep-Deprived Past Bedtime Flag |
| EM | Employee Counter (Index Increment) |
| ETX | Shift End Time Counter |
| J | Shift Index Counter |
| MAXWAKE | Latest Normal Wake time |
| MEAN | Average Alertness |
| MINWAKE | Earliest Normal Wake time |
| MULTIPLIER | Selects Alertness Graph Curve |
| N | Normal Alertness Value for Current Period |
| NB | Normal Bedtime |
| NBX | Normal Bedtime Index |
| NF | Normal Sleep Schedule Factor |
| NW | Normal Wake time |
| NWX | Normal Wake time Index |
| PA | Phase Advance Counter |
| PI | Phase Index |
| PL | Phase Lag Counter |
| PS | Phase Shift in ½ hour ticks |
| S | Shift Number |
| SHT | Shift Time Array |
| SL | Shift Length |
| SLD | Sleep Duration |
| SLDX | Sleep Duration Factor Index |
| SLF | Sleep Factor |
| SLRF | Sleep Restriction Multiplier Array |
| ST | Shift Start Time |
| STX | Shift Start Time Index |
| TIME | Time-of-Day Array |
| TODF | Time-of-Day Factor Array |
| TTB | Time Until Normal Bedtime in ½ hour ticks |

These descriptions will be further elaborated upon in the detailed description which follows.

FIGURE 7A

Figure 7A:
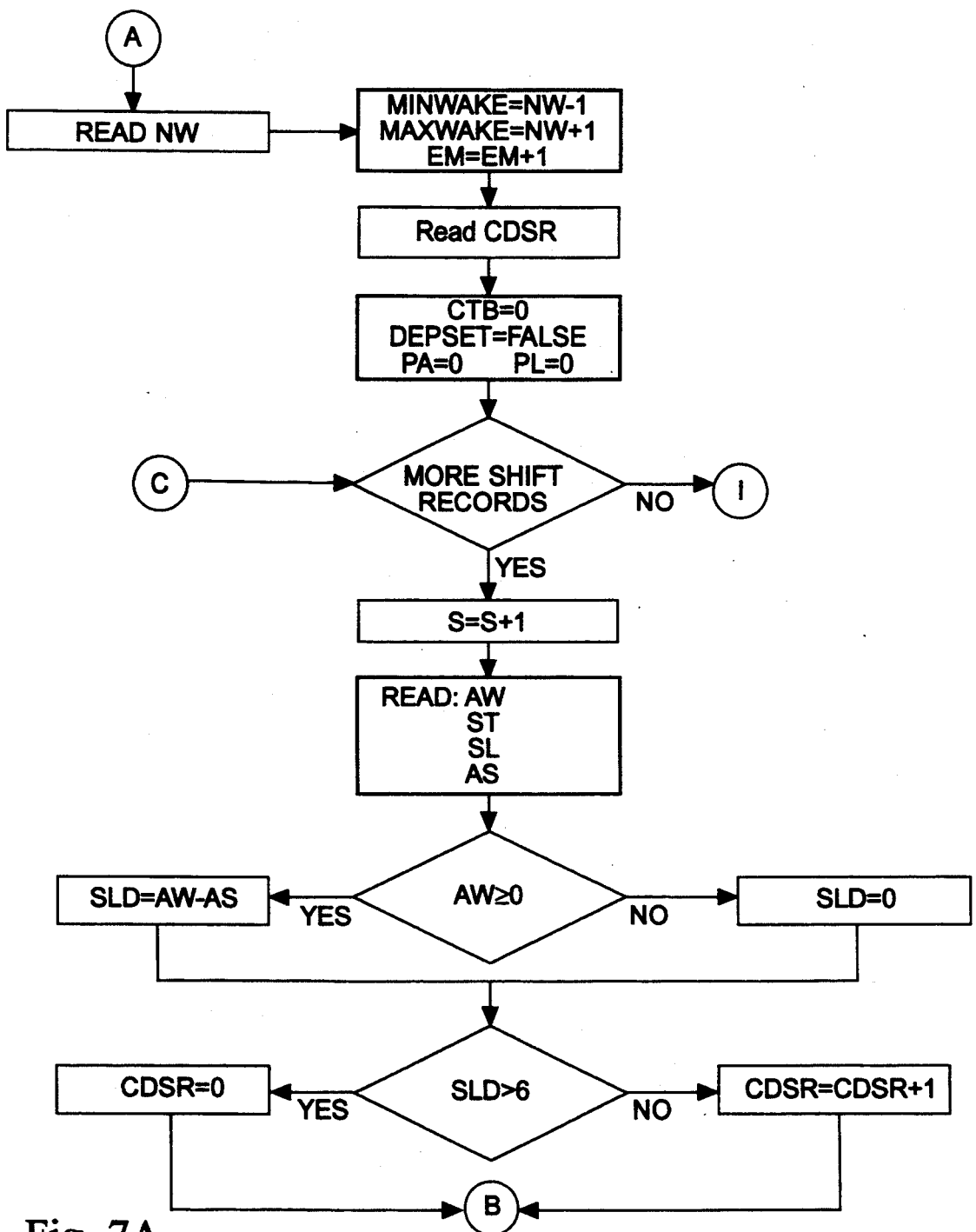
FIGS. 7A–7H show a method of determining the Modified Baseline Alertness Curve (MBAC) for a worker, by the application of Alertness Modifying Stimulus (AMS) factors to the BAC.

Referring first to FIG. 7A, beginning at letter A, the normal wake-up time (NW) for a worker is read. This value represents the normal wake-up time in the residence time zone for the worker. This time is assumed to be in the range between 5 and 8 AM. It is not necessarily the actual time of wake-up for the worker, but it is the time the worker would normally arise were he or she living according to a "normal" schedule in the local time zone.

The minimum and maximum wake-up times (MIN-WAKE and MAXWAKE) are set to one hour before and one hour after the normal wake-up time. These values will be used later for determining whether or not a phase shift due to sleep out-of-phase has occurred. The employee counter (EM) is then incremented so that the data can be stored in the multidimensional results array (described later).

The consecutive number of days of sleep restriction (CDSR) is then read. This number will be zero unless, prior to the beginning of the simulation, the worker had slept for a period of less than six hours, in which case the number of consecutive days of such reduced sleep is input here. Note that consolidated sleep of more than 6 hours on any day will cause CDSR to be reset to zero.

Miscellaneous flags and counters are then reset. (The function of these variables and counters is explained at their point of initial use.)

If this is not the first iteration of the program module, a test is made to see if any further shift records exist for the worker being analyzed. If not, control is transferred to the logic illustrated in FIG. 7H, which is explained later. Otherwise, the shift counter (S) is incremented, and the next (or first) shift record is read for the worker. This record contains the following information:

| | |
|---|---|
| AW | This is the actual time the worker woke up prior to beginning the work shift. This information can be from a diary provided by the worker, from normative data for workers on a given schedule, or it can be estimated based on shift start time as compared to normal wake time in the time zone, in order to arrive at a reasonable estimate. Obviously, the more accurate the data, the more accurate the prediction. Consequently, reliable diary data is preferable over other sources. AW can also be set to a negative number, indicating that prior to the beginning of the simulation, the worker had not slept in the preceding 24 hour period. |
| ST | This is the shift start time for the shift being evaluated. For example, 8:30 AM is shown as 8.5. The shift may be one actually worked (for historical analysis), or a shift planned to be worked. |
| SL | This is the shift length in hours. |
| AS | This is the time of actual sleep onset time for the sleep period which preceded the shift being evaluated. It is, by definition, a time prior to the AW (actual wake time) shown above. |

If some sleep occurred in the period prior to the beginning of the shift (AW>=0), the duration of the sleep period (SLD) is computed as the difference between the actual wake time (AW) and the actual sleep onset time (AS). If the worker did not sleep in the day preceding the shift (AW<0), SLD is set to zero.

Following this, a check is made to see if the sleep duration is more than 6 hours. If so, the cumulative number of days of sleep restriction (CDSR) is reset to zero. Otherwise, the value of CDSR is incremented by 1. Control is then transferred to the logic beginning at letter B of FIG. 7B.

FIGURE 7B

The normal bedtime for the worker (NB) is set equal to 7 hours prior to the normal wake-up time (NW). This, however, can be adjusted, should reliable diary data exist. Array index NBX is calculated for the normal bedtime (NB), and array index NWX is calculated for the normal wake time by multiplying these times by 2. These indices will be used to access baseline alertness data for specific times of day.

Next, a test is made to see if the actual wake-up time (AW) is earlier or later than the minimum (MIN-WAKE) and maximum (MAXWAKE) normal wake-up times for the individual. If so, the individual is said to be sleeping out-of-phase, and control is transferred to the logic beginning at letter H of FIG. 7G. This figure is described in detail further on in the explanation.

If the worker is not sleeping out-of-phase, the next step is to compute the index entry value for the shift start time (STX) by multiplying the shift start time (ST) by 2. The Shift End Time counter (ETX) is computed by multiplying the shift length (SL) by 2, then adding it to the shift start time index. ETX will be used to determine when the program has processed through the end of the work shift.

The time until the worker's normal bedtime (TTB) is next computed by subtracting the shift start time index value (STX) from the normal bedtime index entry (NBX) and then applying any phase shift adjustment (PS) due to sleep out-of-phase. This possible phase adjustment is applied in FIG. 7G, described later.

The sleep duration index (SLDX) is computed by multiplying the sleep duration by 2. Then the index counter J is set to the shift start time index STX. This value will be incremented through the shift in half-hour increments until it exceeds the shift end time counter ETX, at which point the next shift is processed by returning control to logic beginning at letter C of FIG. 7A. Otherwise, processing continues at letter D of Figure 7C.

FIGURE 7C

If the value of index counter J is greater than 47, the current period pointer CP is set to this value less 48. This is to ensure that index references fall within the range of the matrices. (All time matrices contain 48 entries, two per hour.) Otherwise the current period pointer CP is set to the value of J.

When the worker is up later than his or her normal bedtime, sleep deprivation becomes a factor. The counter of index ticks until normal bedtime (CTB) is incremented to keep track of how far toward the bedtime the simulation has progressed. When it reaches the value of the time-to-bed counter TTB, the bedtime has been reached and alertness computation is affected. This will be seen in detail in the description of FIG. 7D.

The arrays are loaded based on an assumed normal wake-up time (NW) of 6 AM. In order to compensate for different values of NW, a normal alertness factor NF is computed. This value equals the difference between the specific worker's normal wake-up time as entered and 6 AM. This adjustment count will be applied when the alertness computation is performed.

The Phase Index offset PI is next computed as the value of the current period CP plus the Phase Shift PS, if any, and the normal factor adjustment NF, if any. The value of PI is then adjusted to keep it within the bounds of the matrix by either adding or subtracting 48 from it, depending on its original value.

If the prior night sleep duration SLD is at least 7 hours, the worker has slept a normal amount prior to beginning work. Computation of the alertness level is accomplished using the normal curve according to the processing described beginning at letter E of FIG. 7D. If the actual wake time AW is non-negative, this means that the worker slept at least some amount during the preceding night, although not a sufficient amount to operate without any negative effects the following day. Computation of alertness is, therefore, governed by combining the values of a normal alertness curve and a sleep-deprived alertness curve according to the processing described beginning at letter F of FIG. 7E. Otherwise, the user has had no sleep at all, and processing continues at letter G of FIG. 7F.

FIGURE 7D

Figure 7B:
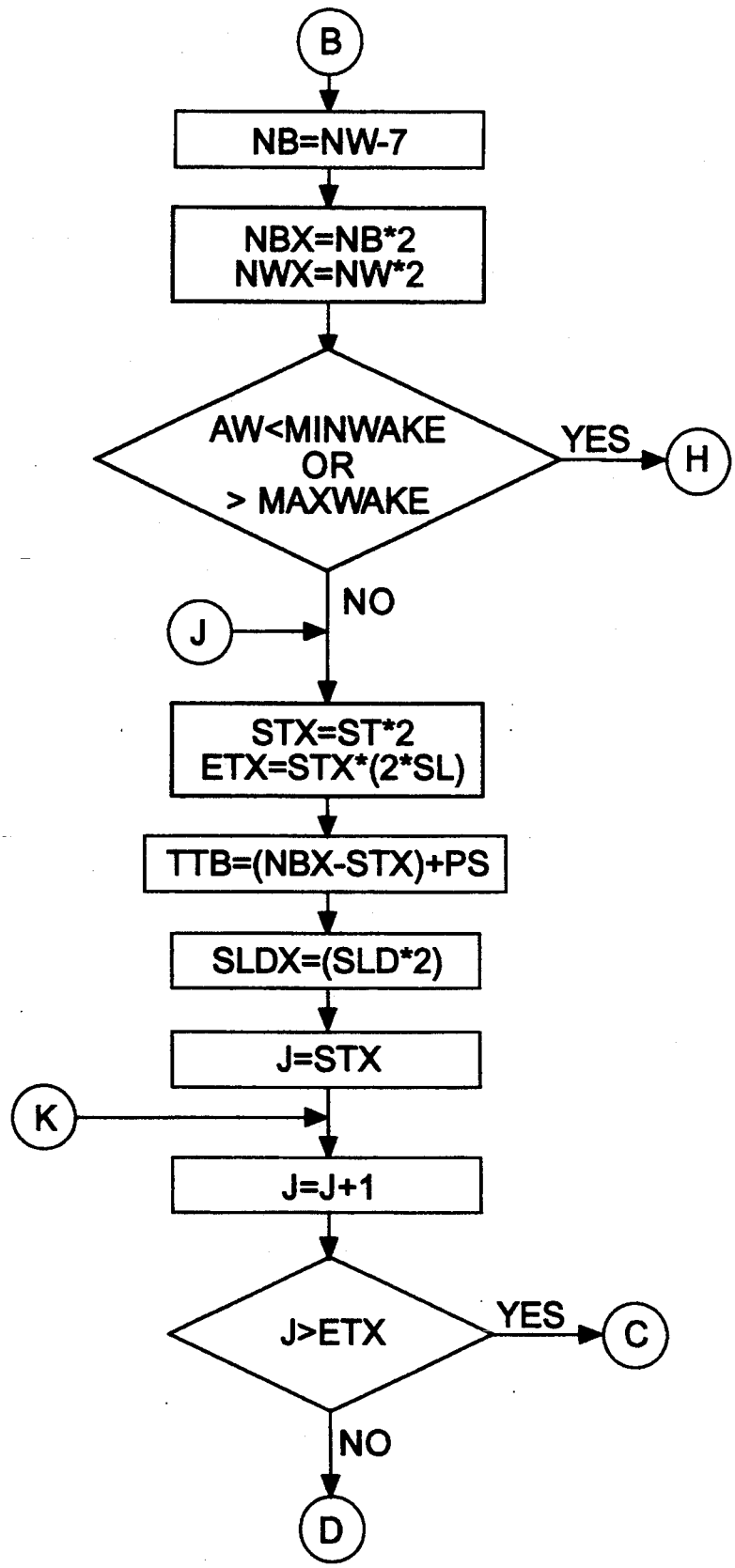
Figure 7C:
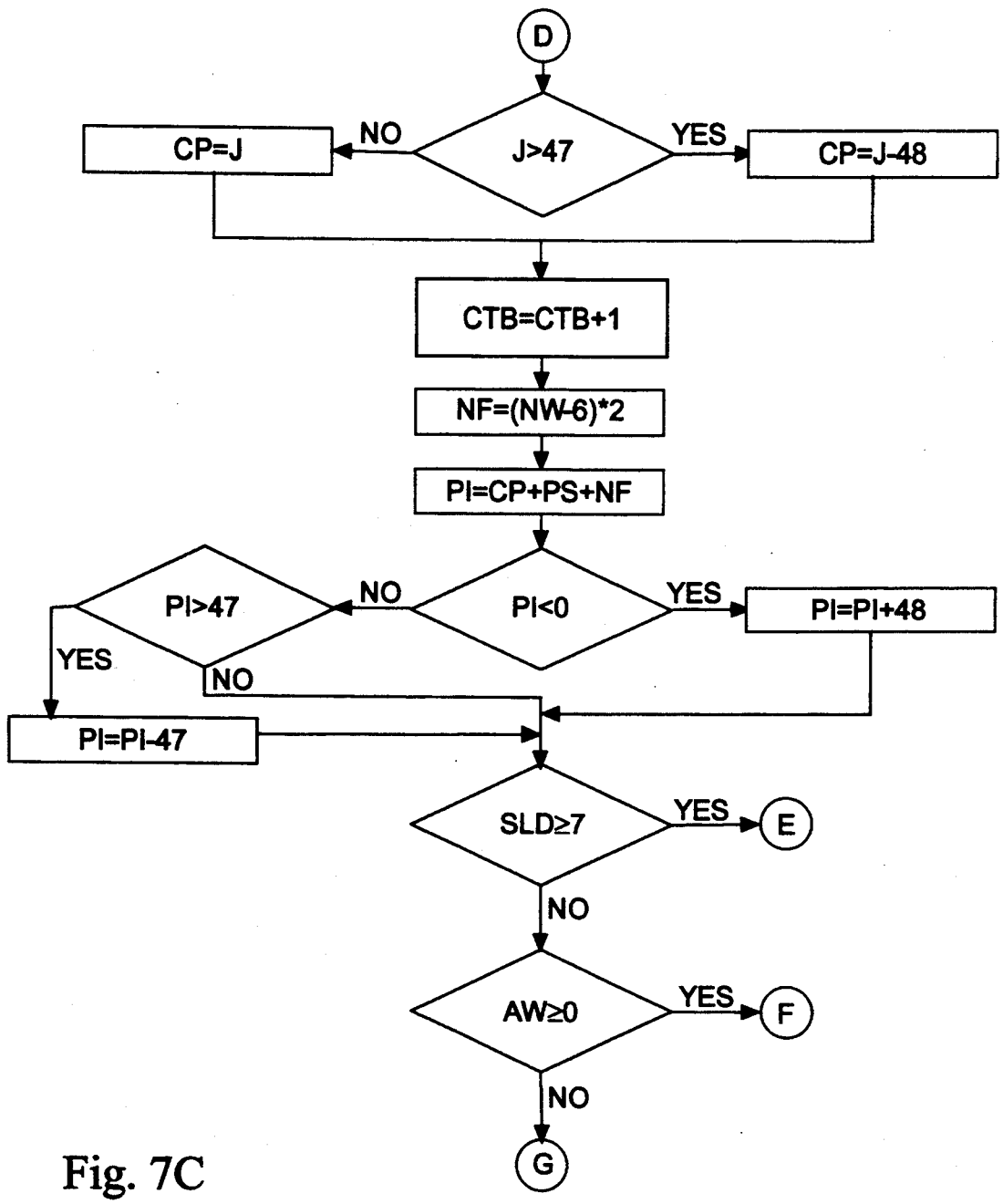
Figure 7D:
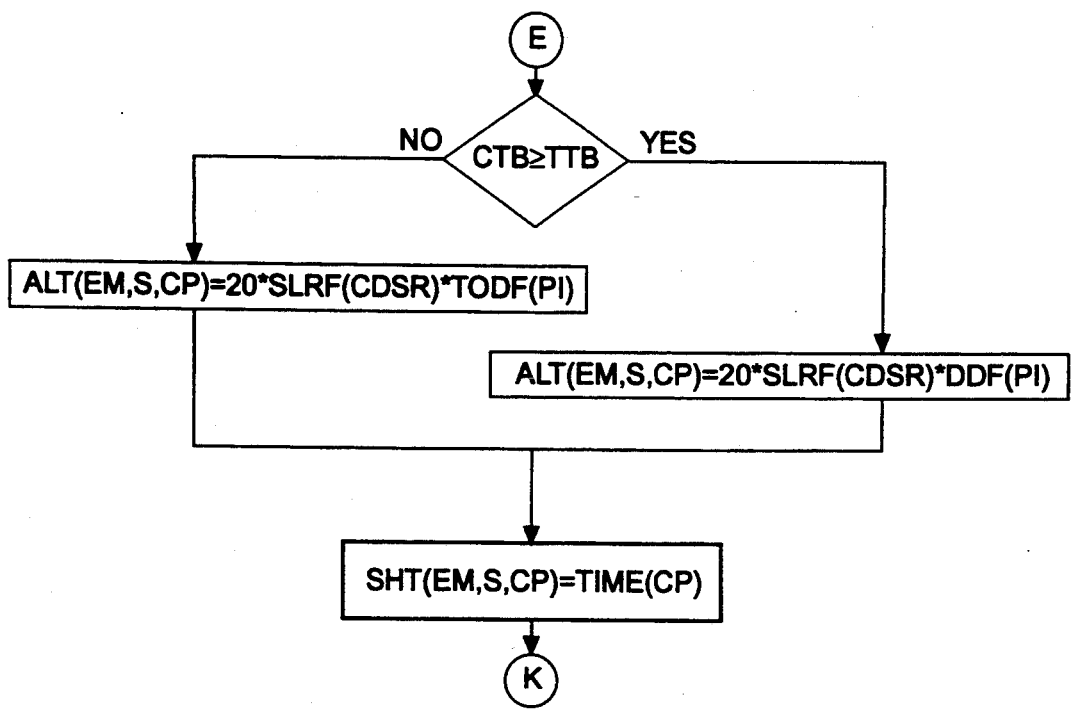

Continuing at letter E of FIG. 7D, the count-to-bedtime counter CTB is compared to the time-to-bedtime counter TTB. If CTB is greater than or equal to TTB, this means that, although the worker slept a sufficient amount prior to beginning work, he is now working beyond his normal bedtime. In this case the alertness level will be calculated using the Deprived Day Factor (DDF) shown in FIG. 6B. The computed alertness level is stored in the alertness array ALT. This array is three dimensional, with the first dimension containing the employee sequence number, the second dimension containing the shift number S, and the third dimension containing the current period CP.

The sleep reduction factor vector SLRF (FIG. 6D) is accessed with the consecutive number of days of sleep restriction CDSR in order to arrive at an adjustment factor. This amount is multiplied by 20 to convert alertness to an MSLT scale. The amount is then multiplied by the value of the Deprived Day Factor (DDF), shown in FIG. 6B, as indexed by the phase index PI. The result is stored in ALT for the current shift S and time period CP.

If the worker is not working past his or her normal bedtime, computation of alertness is accomplished in substantially the same way, except the normal time-of-day factor vector TODF, shown in FIG. 6A, is accessed instead of the Deprived Day Factor.

Following determination of the alertness level for the individual at this point during the shift, the clock time associated with this data point (FIG. 6C) is stored in the Shift Time Matrix SHT, using values from the time vector as indexed by the current period CP. This is useful for subsequent display of the shift data; the corresponding time-of-day is available for presentation along with the alertness values.

Control is then transferred to letter K of FIG. 7B, whereupon the next half-hour period of the shift is processed. This loop continues until alertness has been calculated for all periods within the shift, whereupon the next shift for the employee is processed, keeping the current alertness information as a starting point for the next shift.

FIGURE 7E

Figure 7E:
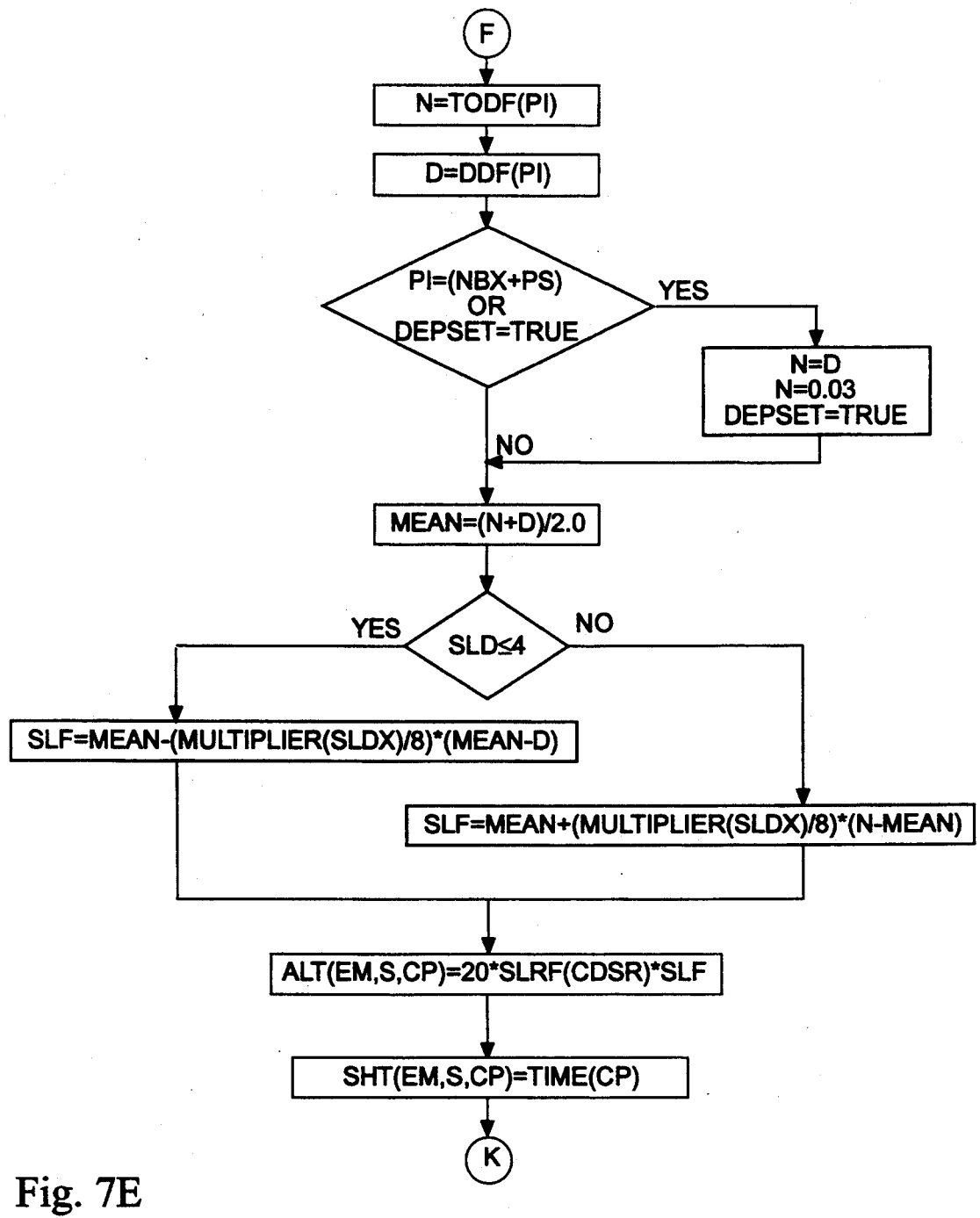
Figure 7F:
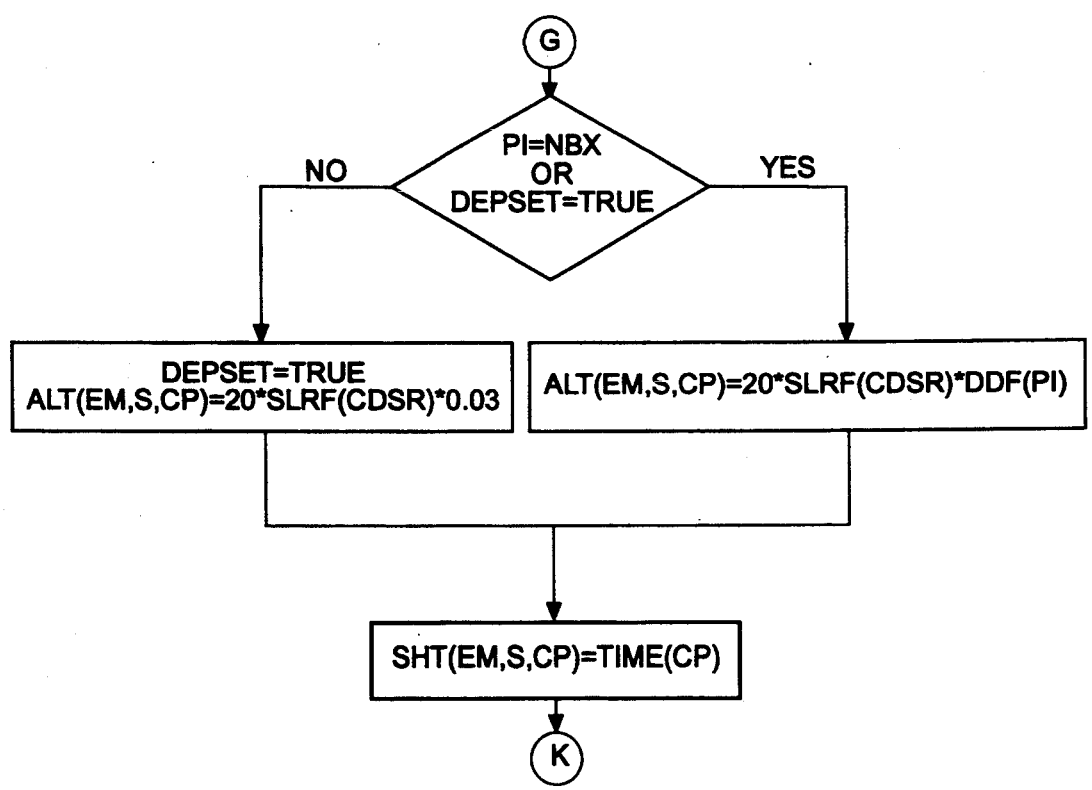
Figure 7G:
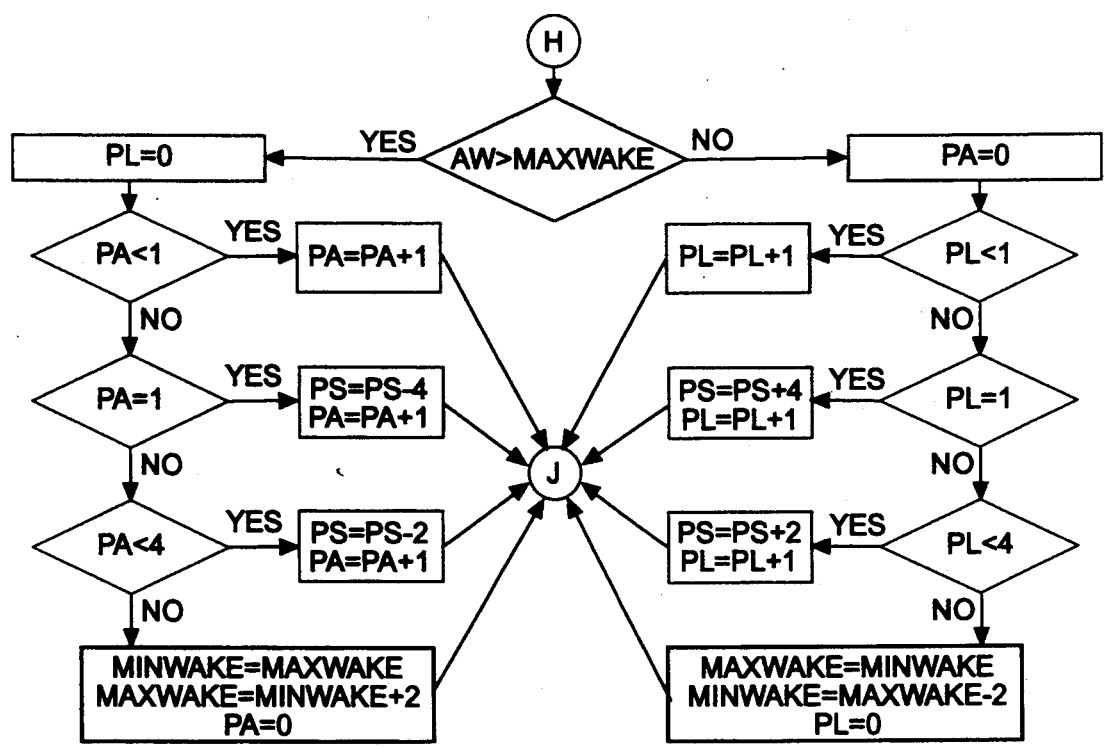

If the worker has slept prior to beginning work, but not an amount considered completely recuperative (7 hours at least), then control is transferred to letter F of FIG. 7E.

A non-sleep deprived alertness value N is retrieved from the normal time-of-day alertness vector TODF (FIG. 6A) according to the value of the phase index PI. A sleep-deprived alertness value D is retrieved from the sleep-deprived alertness vector DDF (FIG. 6B), also according to the value of PI.

If an already sleep deprived person is working through his or her next normal bedtime, the simulation substitutes the deprived value for the normal one, and the lowest alertness level for the deprived value (N=D & D=0.03). There are two checks made to see if this substitution must be made. The first check is simply to see if we are already in the substitution phase (DEPSET=TRUE). If so, the simulation continues to substitute the above values through to the end of the shift. The other check is whether or not the Phase Index (PI) is now equal to the normal bedtime index NBX as adjusted by any phase shift PS. If so, the adjusted normal bedtime has arrived and the worker, already operating on reduced sleep, is now beginning to work through his next bedtime.

Following this, the average (MEAN) of the two alertness values N & D, is computed.

Next, depending on the number of hours the worker slept prior to beginning work, one of sixteen Sleep Factors (SLF) values will be chosen. The sleep factor is the alertness level for the individual prior to adjustment for consecutive days of sleep restriction or conversion to MSLT format.

The multiplier array shown in FIG. 6E is accessed using the Sleep Duration Index, which is set to two times the sleep duration in hours. (e.g. 6 hours sleep=12).

If the previous sleep duration was less than or equal to 4 hours, the "yes" branch is taken and SLF is computed as: MEAN-(MULTIPLIER(SLDX)/8)*-(MEAN-D). Otherwise the "no" branch is taken and SLF is set equal to: MEAN+(MULTIPLIER(SLDX)/8)*(N-MEAN).

Next the Alertness level ALT is computed by applying the Sleep restriction factor SLRF, shown in FIG. 6D, to the previously calculated sleep factor SLF. The clock time for the current period (FIG. 6C) is then stored in the Shift Time matrix (SHT). Control is then transferred to letter K of FIG. 7B, whereupon the next half-hour period of the shift is processed.

FIGURE 7F

If the worker had no sleep prior to beginning work, the worker begins in a sleep-deprived state. If, at this point in the simulation, the worker is working through his normal bedtime (PI=NBX or DEPSET=TRUE), then alertness is set to the minimal value, since the worker, who began work without having slept, has now worked through to his next normal bedtime. If the next normal bedtime for the worker has not yet been reached, then computation of alertness is based on the values found in the Deprived Day Factor (DDF) matrix (FIG. 6B), with the selection being governed by the value of the Phase Index (PI). The clock time for the current period (FIG. 6C) is then stored in the Shift Time matrix (SHT).

Control is then transferred to letter K of FIG. 7B, whereupon the next half-hour period of the shift is processed.

FIGURE 7G

In FIG. 7B, if the actual wake time AW is out of the range of normal wake times as defined by MINWAKE and MAXWAKE, the worker is said to be sleeping out-of-phase, and control is transferred here for evaluation as to whether or not a phase shift should take place.

In the present embodiment, after the second night of sleep out-of-phase, an adjustment of two hours (4 ticks)

is made to the phase shift (PS) index. The direction of the change is determined by whether the worker is awakening later or earlier than normal.

If there is a third or fourth night of sleep out-of-phase, another hour is added or subtracted to PS for each day.

If there is a fifth day of sleep out-of-phase, the minimum normal wake time MINWAKE and maximum normal wake time MAXWAKE are shifted by two hours, in the direction of the wake tendency (i.e. later if arising later, or earlier if arising earlier). The count of nights of sleep out-of-phase is then reset to zero, to enable the process to begin again.

For example, assume a worker now sleeps from 07:00 (7 AM) until 14:00 (2 PM). Previously, the worker's actual wake-up time was 6 AM. This new wake up time is 7 hours later than the previous norm. Since the worker is now is awakening later than standard, the "yes" branch is taken. The phase lag counter PL is reset to 0, the starting point. If the phase advance counter PA is 0, it is simply incremented. If this shift represents work following the second night of sleep out-of-phase for the worker (PA=1), the phase shift index PS is decremented by two hours (4 ticks). This will cause access to the alertness arrays to be backed up by two hours, since the alertness curve will be advanced by two hours. (For example, the early afternoon dip in alertness commonly known as the post-lunch dip, would occur two hours later for this worker.) After both the third (PA=2) and fourth (PA=3) nights of sleep out of phase, an additional hour is added or subtracted to the phase shift index, depending on the direction of the On the fifth day of sleep out-of-phase (PA=4), the actual normal range for this worker is altered. In the present example, MINWAKE is set to the prior value of MAXWAKE, which is 7, and MAXWAKE is incremented by 2 hours to 9.

FIGURE 7H

Figure 7H:
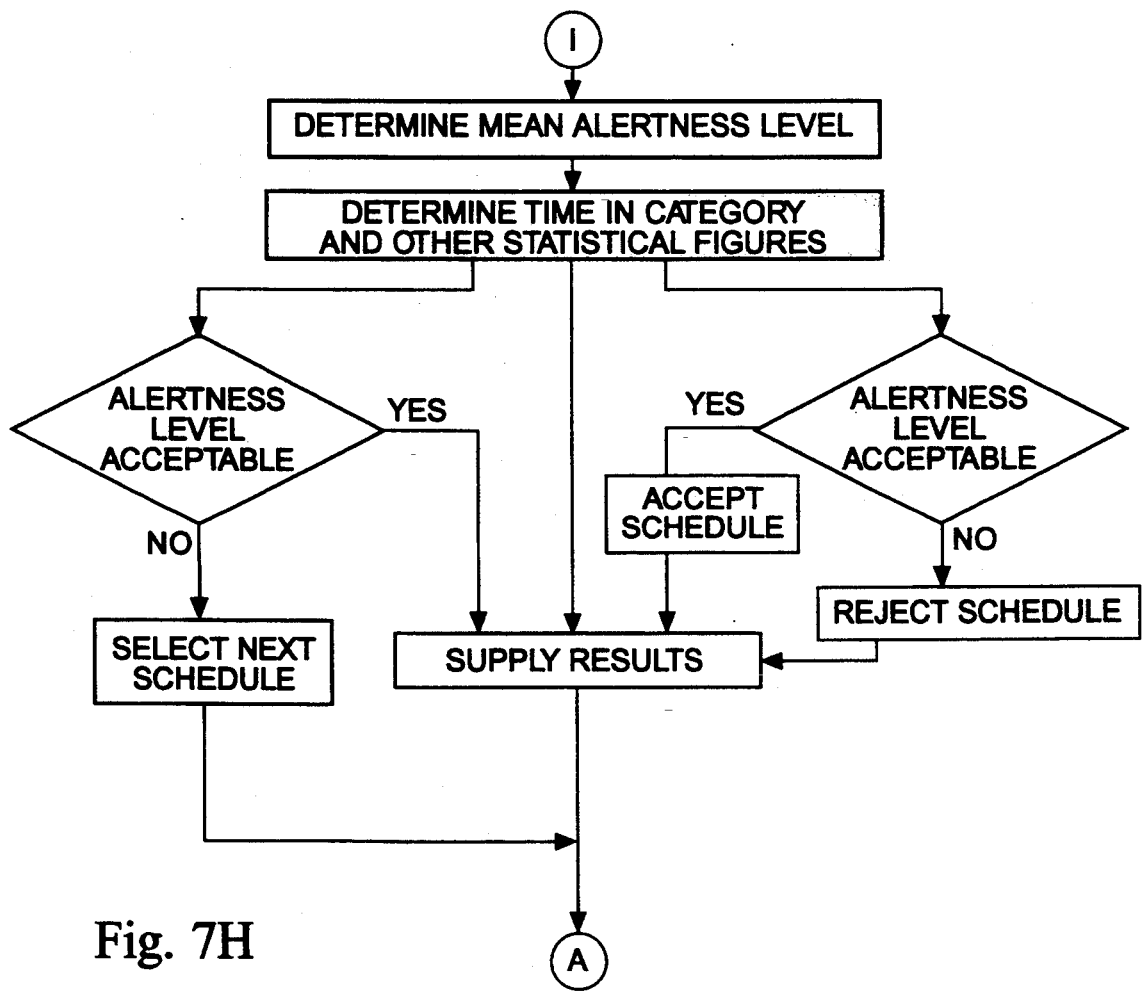

Control is transferred to FIG. 7H when no further shift records exist for the worker being studied. At this point, complete alertness results data exists in the matrix ALT. Depending on the requirements, and using conventional techniques, the mean alertness level, and other statistically significant values are calculated. Preferably, the time spent in each of the four alertness levels is determined. The alertness level is then compared to a minimum value to determine if the schedule worked (or to be worked) meets alertness requirements. For example, a mean alertness level of at least 10 can be required for a shift to be considered acceptable for the individual. Alternatively, time spent below level 5 can be mandated not to exceed a given amount, such as 15% of total shift time, for the schedule to be deemed acceptable.

If the alertness level is not acceptable, another proposed schedule is selected for evaluation, and control passed back into the modeling procedure as shown or the schedule can simply be flagged to be rejected as biologically incompatible with the worker.

The results of the simulation are then supplied to a file and/or a print device to indicate the suitability of using the worker for a specific shift.

FIGURE 8—WORKER SCHEDULE SELECTION

Figure 8:
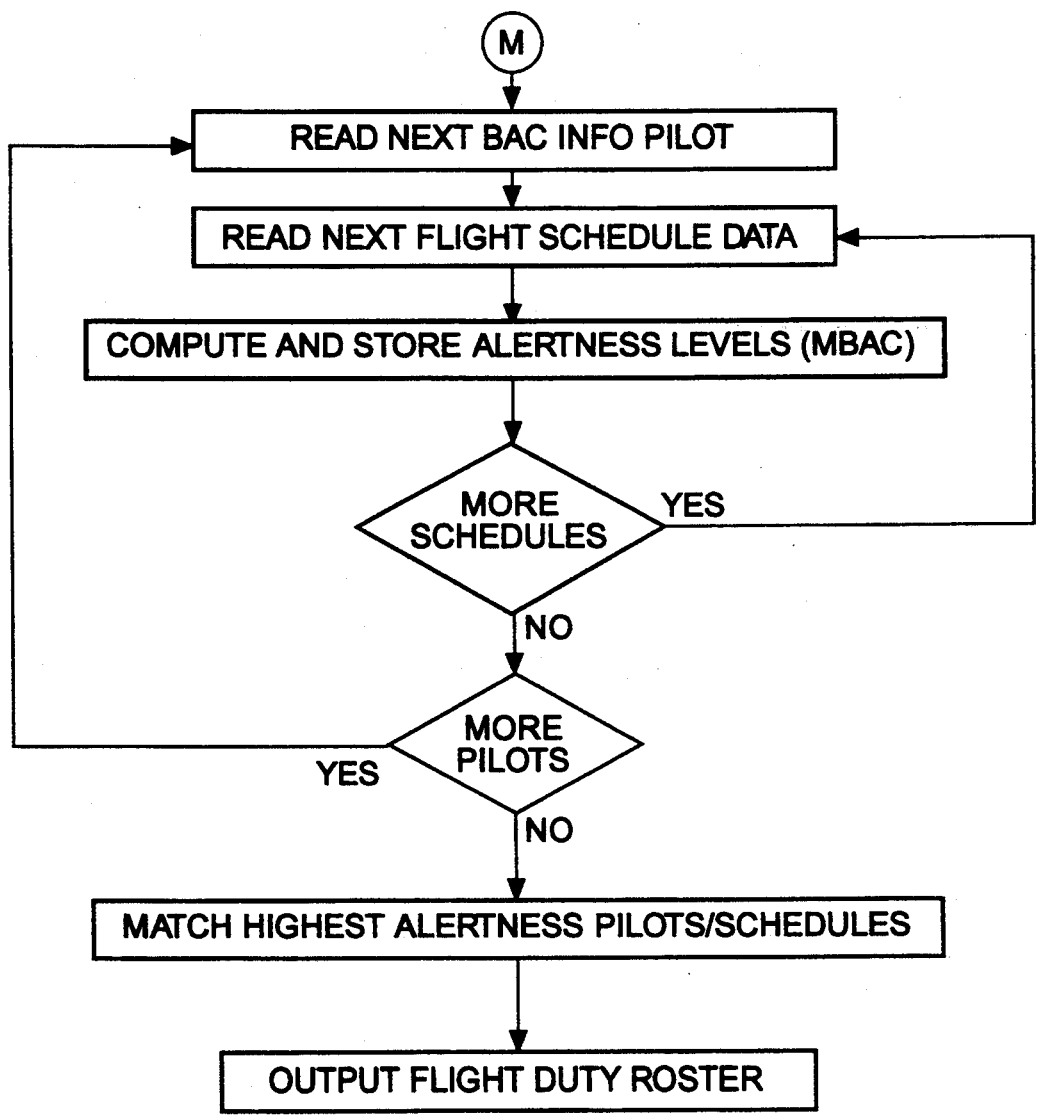
FIG. 8 illustrates a method of selecting a bio-compatible schedule for a worker in accordance with the invention.

FIG. 8 shows one method of incorporating the circadian alertness methodology into a worker scheduling system. The example is for a airline pilot, although the method can be applied to the scheduling of any group of tasks with any group of workers. Beginning at letter M, baseline alertness data is read for a pilot. A proposed flight is next read. Following this, the predicted alertness level for the pilot on the proposed schedule is computed and stored. A check is then made to see if there are more schedules within the group of those to be analyzed. If so, the next schedule is read, and alertness for the pilot is once again computed and stored. Other normal scheduling considerations are included but not shown, since they are commonly known to those skilled in the art of automated schedule processing.

After all schedules have been processed for the first pilot, a check is made to see if there are other pilots within the group of those to be analyzed. If so, control is transferred to the top box and baseline alertness data is read for the next pilot. Computation of the projected alertness level for all schedules is then made for this next pilot.

The processing continues in this fashion until alertness data has been computed for all schedules for each pilot. When there are no further pilots to process, the schedule yielding the highest alertness score for each pilot is matched to that pilot, and a duty roster of flight assignments is output.

CONCLUSIONS, RAMIFICATIONS, AND SCOPE

It will be thus apparent that the circadian alertness simulation method we have invented is useful in order to estimate the probable level of alertness, or conversely, the probable level of drowsiness/sleepiness, of an individual, either as a prediction in advance of undertaking a work schedule, as a reconstruction after the work schedule has been undertaken, or potentially, even in real time during the performance of a work shift.

The method can be used to evaluate possible candidate schedules to determine which of them are going to be more advantageous as compared to others in terms of alertness.

Undesirable schedules generated by a scheduling process, such as in pilot bid packs, and computerized work scheduling systems, can be screened out when their biological effect is determined to be unacceptable or potentially unacceptable.

This method can be adapted to enable development of bio-compatible flight bid packs where an assumed BAC is used as a starting point (e.g. pilot on Eastern Standard Time) and where flights are included in the pack which enable maintenance of a high level of alertness.

The decision of which flight to assign to which pilot would, of course, include many other factors, such as regulatory restrictions, equipment competency, seniority, etc. Use of alertness data, however, assures that flights are assigned to pilots during those periods when they are predicted to be most alert.

The method can also be used to evaluate, either for regulatory or legal purposes, whether particular schedules put people in undue danger of fatigue and the consequent accidents.

This method can further be used to assess which individual employee might be assigned to a particular work duty period when there is a pool of employees available. For example, amongst a group of railroad engineers who are waiting for a train to take out, the method can determine which persons should go out and onto which trains.

A company's performance in terms of their management of human resources and their optimizing of their human resources can also be undertaken through the use of our method. By determining what percentage of time they are operating with people in an impaired state versus a non-impaired state, various corporate strategies can be designed for personnel needs.

A company can also use this method to decide how many people they would need to hire in a particular situation to ensure adequate staffing with non-alertness impaired individuals.

The methodology can also be used to analyze retrospectively the fatigue risks in any given operation and to reconstruct particular events or accidents to determine the likelihood that fatigue played a role.

The methodology described can also allow for the incorporation of other alertness-modifying stimuli, not yet discovered. The values in the arrays can be changed to allow for new findings, differences between worker populations, greater granularity, etc.

The methodology can be used to interface with existing scheduling programs in such a way as to permit the selection or validation of schedules based on the teachings of this disclosure.

Therefore, as can be seen from the above examples, the methodology which we have developed can be used in a myriad of circumstances where determination of one or more subject's alertness level at a given point in time is desired.

Others can, by applying current knowledge, readily modify and/or adapt this embodiment for various applications without departing from the generic concept, and therefore, such other adaptations and modifications should and are intended to be comprehended within the meaning and range of equivalents of the disclosed invention. For example, the organization and values used in the arrays can be changed to reflect new findings, or differences between worker populations. Other factors may be added, and the weighting given to various factors can be changed. The source of alertness data need not be MSLT-based, but can be from any alertness measurement source now known or which may be developed in the future. Additionally, it is to be understood that the phraseology or terminology used is for the purpose of description and not of limitation. Therefore, the scope of this invention should be determined by the appended claims and their legal equivalents and not by the examples given.

We claim:

1. A method of predicting the alertness of an individual, said method comprising the steps of receiving a plurality of initial alertness data of said individual, adjusting said initial alertness data based upon a plurality of predetermined alertness-modifying stimuli to which said individual is exposed, computing data representative of the predicted alertness level for said individual based upon said adjusting of said initial alertness data, and providing said predicted alertness level data in a processable format, said processable format selected from the group consisting of humanly-sensible and machine-readable formats.

2. The method of claim 1 wherein said receiving said plurality of initial alertness data of said individual comprises receiving a plurality of data selected from the group consisting of age, home time zone, morning/evening tendency, sleep/wake diary data, currently acclimatized shift/sleep schedule, shift/duty times, and rules for probable sleep-wake pattern.

3. The method of claim 1 wherein said adjusting said initial alertness data based upon a plurality of predetermined alertness-modifying stimuli to which said individual is exposed comprises adjusting alertness-modifying stimuli selected from the group consisting of nap, caffeine ingestion, alcohol ingestion, sleep deprivation, sleep restriction, photostimulation, sleep phase, and bright light.

4. The method of claim 1 wherein said providing said predicted alertness level data in a humanly-sensible format consists of providing said data as printed output.

5. The method of claim 1 wherein said providing said predicted alertness level data in a machine-readable format consists of providing said data as electronic impulses.

6. A method for determining the bio-compatibility of a given work schedule for an individual, said method comprising the steps of receiving a plurality of initial alertness data of said individual, adjusting said initial alertness data based upon a plurality of predetermined alertness-modifying stimuli to which said individual is exposed, computing modified alertness data for said individual based upon said adjustments to said initial alertness data, determining the bio-compatibility of said work schedule by comparing said modified alertness data during said proposed work schedule to a minimum acceptable alertness level, and supplying said determination in a processable format, said processable format selected from the group consisting of humanly-sensible and machine-readable formats.

7. The method of claim 6 wherein said receiving said plurality of initial alertness data of said individual comprises receiving a plurality of data selected from the group consisting of age, home time zone, morning/evening tendency, sleep/wake diary data, currently acclimatized shift/sleep schedule, shift/duty times, and rules for probable sleep-wake pattern.

8. The method of claim 6 wherein said adjusting said initial alertness data based upon a plurality of predetermined alertness-modifying stimuli to which said individual is exposed comprises adjusting alertness-modifying stimuli selected from the group consisting of nap, caffeine ingestion, alcohol ingestion, sleep deprivation, sleep restriction, photostimulation, sleep phase, and bright light.

9. The method of claim 6 wherein said supplying said determination in a humanly-sensible format consists of supplying said determination as printed output.

10. The method of claim 6 wherein said supplying said determination in a machine-readable format consists of supplying said determination as electronic impulses.

11. The method for selecting a bio-compatible work schedule for an individual, said method comprising the steps of receiving initial alertness data of said individual, receiving at least one proposed schedule for said individual, adjusting said initial alertness data based upon a plurality of predetermined alertness-modifying stimuli to which said individual is exposed, computing modified alertness data for said individual based upon said adjusting of said initial alertness data, selecting said bio-compatible work schedule based on said modified alertness data, and supplying said selection determination in a processable format, said processable format selected from the group consisting of humanly-sensible and machine-readable formats.

12. The method of claim 11 wherein said receiving said plurality of initial alertness data of said individual comprises receiving a plurality of data selected from the group consisting of age, home time zone, morning/evening tendency, sleep/wake diary data, currently acclimatized shift/sleep schedule, shift/duty times, and rules for probable sleep-wake pattern.

13. The method of claim 11 wherein said adjusting said initial alertness data based upon a plurality of predetermined alertness-modifying stimuli to which said individual is exposed comprises adjusting alertness-modifying stimuli selected from the group consisting of nap, caffeine ingestion, alcohol ingestion, sleep deprivation, sleep restriction, photostimulation, sleep phase, and bright light.

14. The method of claim 11 wherein said supplying said selection determination in a humanly-sensible format consists of supplying said selection determination as printed output.

15. The method of claim 11 wherein said supplying said selection determination in a machine-readable format consists of supplying said selection determination as electronic impluses.

* * * * *